US00PP35276P3

(12) United States Plant Patent
Olesen

(10) Patent No.: US PP35,276 P3
(45) Date of Patent: Jul. 25, 2023

(54) HYBRID TEA ROSE PLANT NAMED 'POULREN039'

(50) Latin Name: *Rosa hybrida*
Varietal Denomination: Poulren039

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/803,610

(22) Filed: Sep. 13, 2022

(65) Prior Publication Data

US 2023/0103290 P1 Mar. 30, 2023

(30) Foreign Application Priority Data

Sep. 24, 2021 (QZ) ..... PBR 2021/2354

(51) Int. Cl.
*A01H 5/02* (2018.01)
*A01H 6/74* (2018.01)

(52) U.S. Cl.
USPC ..... Plt./137
CPC ..... *A01H 6/749* (2018.05)

(58) Field of Classification Search
USPC ..... Plt./101, 130, 137
See application file for complete search history.

*Primary Examiner* — Susan McCormick Ewoldt

(57) ABSTRACT

A new garden rose plant of the Hybrid Tea class which has abundant, pink flowers and attractive foliage. This new and distinct variety has shown to be uniform and stable in the resulting generations from asexual propagation.

2 Drawing Sheets

Botanical designation: *Rosa hybrida.*

Variety denomination: 'Poulren039'.

This application claims priority to Plant Breeder's Rights Application Number 2021/2354, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulren039', originated as a single seedling from the stated cross.

The new variety may be distinguished from its male pollen parent and female seed parent primarily by the following characteristics. While flowers of the male pollen parent plant have about 65 petals, the new variety has 145 flower petals. The female seed parent plant has light pink flowers while the new variety has pink flowers.

The objective of the hybridization of this rose variety was to create a new and distinct variety with unique qualities, such as:

1. Uniform and abundant pink flowers;
2. Vigorous, but compact growth when propagated on its own roots;
3. Exceptional disease resistance; and
4. Strong flower fragrance.

This combination of qualities is not present in previously available commercial cultivars of this type, known to the inventor, and distinguish 'Poulren039' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulren039' was selected in the spring of 2014 by the inventor as a single plant from the progeny of the aforementioned hybridization.

Asexual reproduction of 'Poulren039' by rooted cuttings was first done by Mogens N. Olesen in the nursery in Fredensborg, Denmark in July, 2014. This initial and other subsequent asexual propagations conducted in controlled environments have demonstrated that the characteristics of 'Poulren039' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren039'.

Specifically illustrated in FIG. 1 of the drawings are juvenile bare stem exhibiting small and large prickles, juvenile leaves, mature stem and leaves, flower petals detached, and sepals attached to receptacle.

Figure 1:
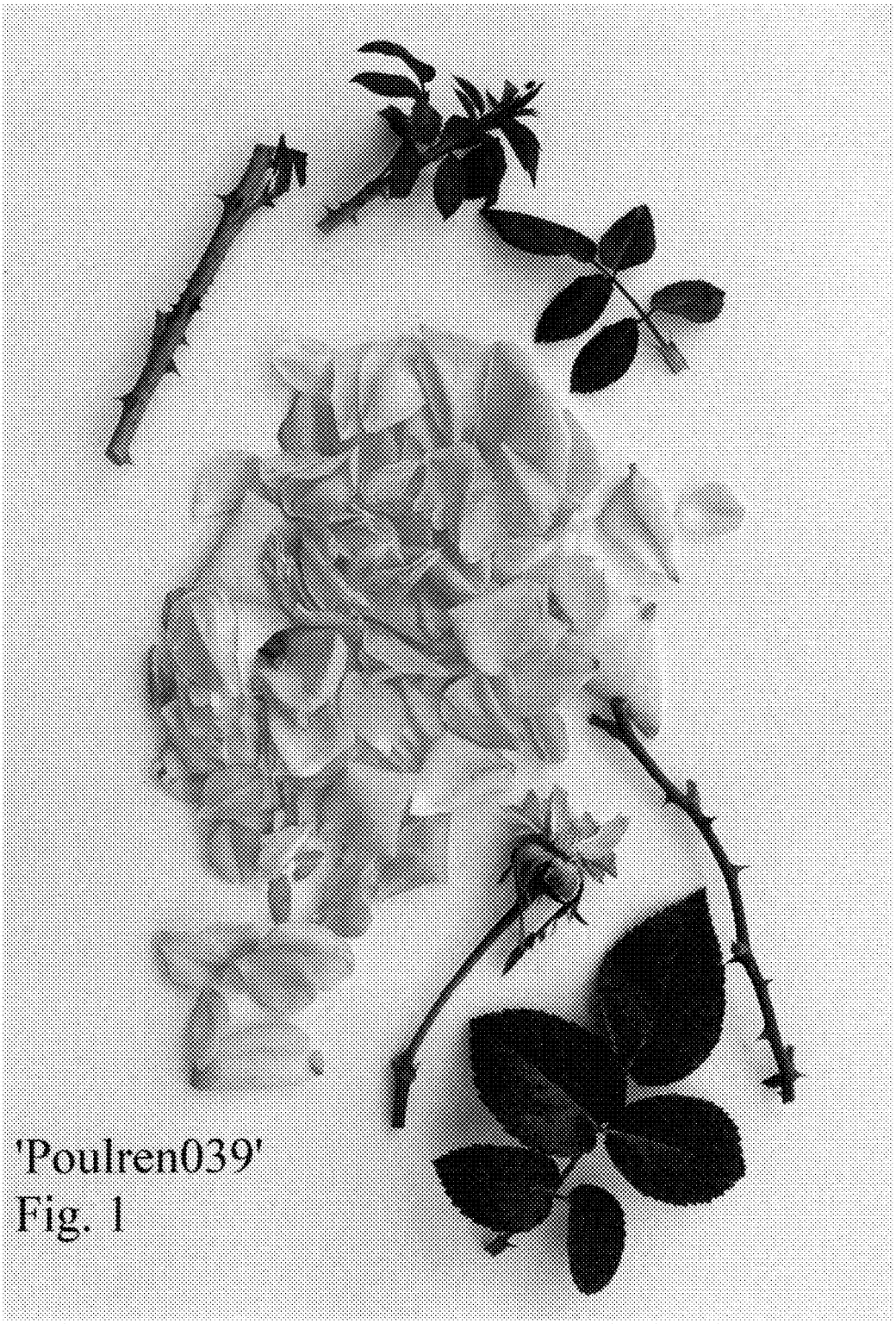
Figure 2:
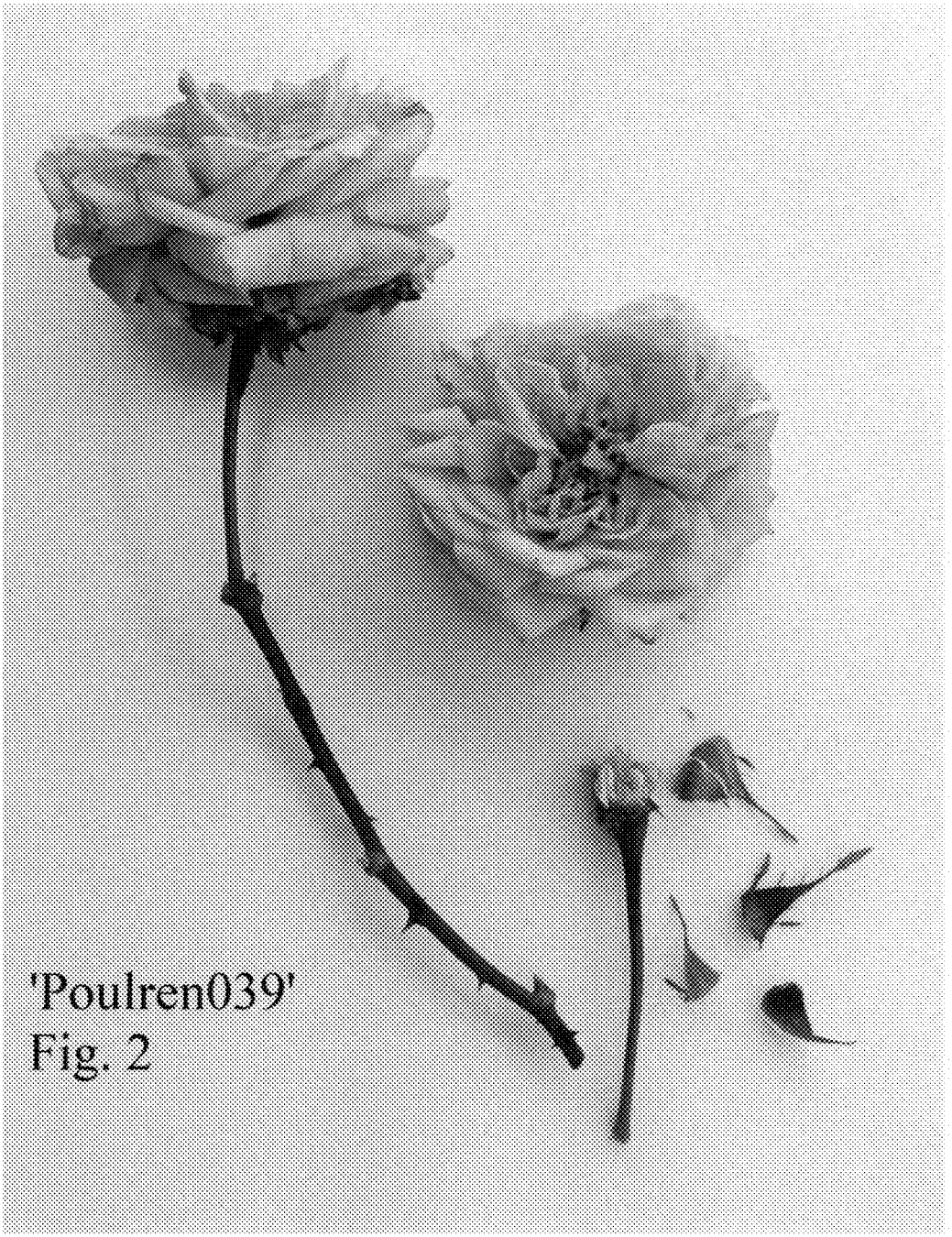

Specifically illustrated in FIG. 2 of the drawings are open flowers viewed from above and the side, and sepals detached revealing reproductive flower parts. Plants shown are 2 years of age.

DETAILED DESCRIPTION OF THE VARIETY

The following is a description of 'Poulren039', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulren023', U.S. Plant Pat. No. 27,656 are now compared to 'Poulren039'. The claimed plant has 145 petals with a flower diameter of 85 mm. The comparison variety has 25 to 30 petals with a flower diameter of 105 mm. In terms of general tonality of flower, the comparison variety is Red Group 49A and Red-Purple Group 62D. General flower tonality of the claimed plant is Red Group 55C and Red Group 52C.

FLOWER AND FLOWER BUD

Blooming habit: Continuous.

Flower bud:

- *Size.*—Upon opening, 20 mm in length from base of receptacle to end of bud. Bud diameter is 13 mm.
- *Bud form.*—Urceolate.
- *Sepal inner surface.*—Color: Yellow-Green Group 146D with strong intonations of Greyed-Orange Group 166A. Surface: Lightly pubescent.
- *Sepal outer surface.*—Color: Yellow-Green Group 144A with strong intonations of Greyed-Red Group 178A. Texture: Rough with stipitate glands.
- *Sepal shape.*—Apex: Cirrhose. Base: Flat at union with receptacle.
- *Sepal margin.*—Margins have strong foliaceous appendages on three of the five sepals.
- *Sepal size.*—About 50 mm long, 11 mm wide.
- *Receptacle.*—Texture: Smooth. Size: 10 mm in height, 10 mm wide. Color: Yellow-Green Group 144A with intonations of Greyed-Red Group 180A. Shape: Funnel.
- *Pedicel.*—Surface: Smooth. Length: 65 mm. Diameter: 3 mm on average. Color: Yellow-Green Group 144A with intonations of Greyed-Red Group 180A. Strength: Strong.

Flower bud development: Flower buds are borne singly.

Flower bloom:

- *Fragrance.*—Strong perfume.
- *Duration.*—The blooms have a duration on the plant of approximately 14 days. Petals fall cleanly away from plant after flowers have fully matured.
- *Size.*—Flower diameter is 85 mm when open. Flower depth is 41 mm.
- *Flower shape.*—Open cup, very double flower, with petals that curve out from the center.
- *Shape of flower, side view.*—The upper portion is flat. The lower portion is concave.

Petalage: Under normal conditions, flowers have about 145 petals.

General tonality of flower: Open flowers are Red Group 55C and Red Group 52C.

Petal color:

- *Upon opening and after opening, outer and inner petals.*—Upper surface: Red-Purple Group 62B. Lower surface: Red-Purple Group 62C.
- *Upon opening, inner petals.*—Upper surface: Yellow Group 5B at the basal zone. Red Group 43B at the middle and marginal zone. Lower surface: Red Group 46C with streaks of Red Group 56C. Yellow Group 4B at the basal zone.

Petals:

- *Petal reflex.*—Strong, bilateral reflex.
- *Margin.*—Entire and uniform. Moderate undulations.
- *Shape.*—Broad and elliptic. Apex shape: Rounded. Base shape: Acute.
- *Size.*—45 mm (l)×36 mm (w).
- *Texture.*—Smooth.
- *Thickness.*—Average.

Petaloids:

- *Size.*—15 mm (l) by 10 mm (w).
- *Quantity.*—About 35.
- *Shape.*—Elliptical with an acute base and rounded apices. Many petaloids are fused with anthers and filaments.
- *Margins.*—Small cleft on the apex.
- *Color.*—Red-Purple Group 62B on the upper and lower surface, with a petal spot of Yellow Group 4B at the basal zone.

Reproductive flower parts:

- *Pollen.*—None observed.
- *Anthers.*—Size: 2 mm in length. Color: Greyed-Yellow Group 160D. Quantity: 42 on average.
- *Filaments.*—Color: White Group 155A. Length: 4 mm.
- *Pistils.*—Length: 11 mm. Quantity: 30 on average.
- *Stigmas.*—Color: Orange-White Group 159C.
- *Styles.*—Color: Yellow-Green Group 145D.
- *Location of stigmas.*—Superior in location relative to the length of the filaments and the height of the anthers.
- *Hips.*—None Observed.

PLANT

Plant growth: Upright Plants are 35 cm in height, and 39 cm wide.

Stems:

- *Color of juvenile growth.*—Yellow-Green Group 145A.
- *Color of mature growth.*—Yellow-Green Group 147A.
- *Length.*—Canes are about 18 cm from the base of the plant to the flowering portion.
- *Diameter.*—About 4 to 7 mm.
- *Internodes.*—On mature canes about 50 mm between nodes.
- *Surface texture.*—Young wood: Rough with many small prickles. Older wood: Smooth.

Long prickles:

- *Incidence.*—10 prickles per 10 cm of stem.
- *Size.*—Average length of prickles on mature stems is 7 mm.
- *Shape.*—Upper portion is linear. Lower portion is concave.
- *Color.*—Juvenile prickles: Greyed-Purple Group 184A. Mature prickles: Greyed-Purple Group 183C.

Plant foliage:

- *Compound leaf.*—165 mm (l)×140 (w).
- *Quantity.*—2 leaves per 10 cm of stem on average.
- *Leaf bearing angle to the stem.*—45 degrees.
- *Color of juvenile foliage.*—Upper side: Yellow-Green Group 146B with intonations of Greyed-Purple Group 187A. Lower side: Greyed-Purple Group 187A.
- *Color of mature foliage.*—Upper side: Yellow-Green Group 147A. Lower side: Yellow-Green Group 146B.

Plant leaves and leaflets:

*Stipules*.—Size: 14 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 30 mm. Diameter: 2 mm. Upper surface color: Yellow-Green Group 144A. Lower surface color: Yellow-Green Group 144A.

*Rachis*.—Length: 50 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 79 mm long, 49 mm wide. Shape: Generally elliptical. Base: Rounded. Apex: Acute. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phraginidium* spp., black spot *Diplocarpon rosae*, and *Botiytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulren039' substantially as described and illustrated herein.

* * * * *

'Poulren039'

'Poulren039'